US007768646B1

(12) United States Patent
Mentzer et al.

(10) Patent No.: US 7,768,646 B1
(45) Date of Patent: Aug. 3, 2010

(54) METHODS AND SYSTEMS FOR DETECTING AND/OR DETERMINING THE CONCENTRATION OF A FLUID

(75) Inventors: Mark A. Mentzer, Lititz, PA (US); Nicholas P. Petrillo, New Cumberland, PA (US); Wayne A. Webb, Lancaster, PA (US)

(73) Assignee: Advanced Precision Inc., Mechanicsburg, PA (US)

( * ) Notice: Subject to any disclaimer, the term of this patent is extended or adjusted under 35 U.S.C. 154(b) by 620 days.

(21) Appl. No.: 11/670,157

(22) Filed: Feb. 1, 2007

(51) Int. Cl.
*G01N 21/00* (2006.01)
(52) U.S. Cl. .................................................. 356/436
(58) Field of Classification Search ........................ None
See application file for complete search history.

(56) References Cited

U.S. PATENT DOCUMENTS

| | | | | |
|---|---|---|---|---|
| 4,201,471 A | * | 5/1980 | Pitt et al. | 356/338 |
| 4,516,432 A | * | 5/1985 | Hironaga et al. | 250/574 |
| 4,627,284 A | * | 12/1986 | Gersh et al. | 250/504 R |
| 4,785,814 A | * | 11/1988 | Kane | 356/41 |
| 4,800,886 A | * | 1/1989 | Nestor | 600/311 |
| 5,152,287 A | * | 10/1992 | Kane | 356/39 |
| 5,193,544 A | * | 3/1993 | Jaffe | 600/323 |
| 5,279,793 A | * | 1/1994 | Glass | 385/13 |
| 6,016,191 A | * | 1/2000 | Ramos et al. | 356/70 |
| 6,831,290 B2 | | 12/2004 | Mentzer | |
| 6,970,247 B2 | * | 11/2005 | Yankielun | 356/436 |
| 2002/0054288 A1 | * | 5/2002 | Kim et al. | 356/317 |
| 2004/0036043 A1 | * | 2/2004 | Murshid | 250/901 |

FOREIGN PATENT DOCUMENTS

GB 2336668 A * 10/1999
JP 03215711 A * 9/1991

OTHER PUBLICATIONS

El-Baradie et al., Optical Selection of the preferred solvent of a standard polymer for laser light scattering phenomena investigations, Physica B 292 (Feb. 2, 2000), pp. 208-212.*
Simpson, J.O. et al., "Fundamental Insight on Developing Low Dielectric Constant Polyimides", *NASA Langley Research Center*, Hampton, VA 23681-0001, 19 pages.
Handbook of Aviation Fuel Properties, CRC Report No. 635, 2004, 3rd edition, 141 pages.
Co-pending U.S. Appl. No. 11/649,109, filed Jan. 3, 2007 and entitled "Method and Systems for Determining the Density and/or Temperature of Fluids".

* cited by examiner

*Primary Examiner*—Gregory J Toatley, Jr.
*Assistant Examiner*—Juan D Valentin
(74) *Attorney, Agent, or Firm*—Smith, Gambrell & Russell, LLP (57) ABSTRACT

Methods and systems detect the presence of a fluid, such as water, based on a reflection of optical energy from the fluid. Methods and systems also determine the concentration of a constituent element in a mixture based on a reflection of optical energy from the mixture.

22 Claims, 12 Drawing Sheets

| Temperature °C | Dielectric Constant $\varepsilon$ | Computed Refractive Index $n = \varepsilon^{1/2}$ n |
|---|---|---|
| -40 | 2.210 | 1.487 |
| -30 | 2.195 | 1.482 |
| -20 | 2.185 | 1.478 |
| -10 | 2.180 | 1.476 |
| 0 | 2.155 | 1.468 |
| 10 | 2.140 | 1.463 |
| 20 | 2.125 | 1.458 |
| 30 | 2.110 | 1.453 |
| 40 | 2.095 | 1.447 |
| 50 | 2.085 | 1.444 |
| 60 | 2.070 | 1.439 |
| 70 | 2.055 | 1.434 |
| 80 | 2.040 | 1.428 |

FIG. 11

| ml Jet-A per Liter in fuel water mix | Water concentration parts per million | ml water per Liter in fuel water mix | Computed refractive index of mix $n_{mix}$ | Computed Fresnel Signal $R_{dB}$ |
|---|---|---|---|---|
| A | B | C | D | E |
| 1000 | 0 | 0 | 1.45770 | -34.00777 |
| 999.999 | 1 | 0.001 | 1.45770 | -34.00775 |
| 999.99 | 10 | 0.01 | 1.45770 | -34.00758 |
| 999.9 | 100 | 0.1 | 1.45769 | -34.00591 |
| 999.8 | 200 | 0.2 | 1.45768 | -34.00404 |
| 999.7 | 300 | 0.3 | 1.45766 | -34.00218 |
| 999.6 | 400 | 0.4 | 1.45765 | -34.00032 |
| 999.5 | 500 | 0.5 | 1.45764 | -34.99846 |
| 999.4 | 600 | 0.6 | 1.45763 | -33.99660 |
| 999.3 | 700 | 0.7 | 1.45761 | -33.99474 |
| 999.2 | 800 | 0.8 | 1.45760 | -33.99288 |
| 999.1 | 900 | 0.9 | 1.45759 | -33.99102 |
| 999 | 1000 | 1 | 1.45758 | -33.98916 |
| 998 | 2000 | 2 | 1.45745 | -33.97058 |
| 997 | 3000 | 3 | 1.45733 | -33.95205 |
| 996 | 4000 | 4 | 1.45720 | -33.93355 |
| 995 | 5000 | 5 | 1.45708 | -33.91509 |
| 994 | 6000 | 6 | 1.45695 | -33.89667 |
| 993 | 7000 | 7 | 1.45683 | -33.87829 |
| 992 | 8000 | 8 | 1.45670 | -33.85994 |
| 991 | 9000 | 9 | 1.45658 | -33.84163 |
| 990 | 10000 | 10 | 1.45645 | -33.82335 |
| 980 | 20000 | 20 | 1.45521 | -33.64262 |
| 970 | 30000 | 30 | 1.45396 | -33.46543 |
| 960 | 40000 | 40 | 1.45271 | -33.29163 |
| 950 | 50000 | 50 | 1.45146 | -33.12110 |
| 940 | 60000 | 60 | 1.45022 | -32.95372 |
| 930 | 70000 | 70 | 1.44897 | -32.78936 |
| 920 | 80000 | 80 | 1.44772 | -32.62793 |
| 910 | 90000 | 90 | 1.44648 | -32.46930 |
| 900 | 100000 | 100 | 1.44523 | -32.31339 |
| 800 | 200000 | 200 | 1.43276 | -30.88515 |
| 700 | 300000 | 300 | 1.42029 | -29.64923 |
| 600 | 400000 | 400 | 1.40782 | -28.55879 |
| 500 | 500000 | 500 | 1.39535 | -27.58226 |
| 400 | 600000 | 600 | 1.38287 | -26.69732 |
| 300 | 700000 | 700 | 1.37040 | -25.88765 |
| 200 | 800000 | 800 | 1.35793 | -25.14090 |
| 100 | 900000 | 900 | 1.34546 | -24.44753 |
| 0 | 1000000 | 1000 | 1.33299 | -23.80004 |

METHODS AND SYSTEMS FOR DETECTING AND/OR DETERMINING THE CONCENTRATION OF A FLUID

TECHNICAL FIELD

The present application relates generally to the detection of fluids. The present application also relates to determining the concentration of a fluid in a mixture.

BACKGROUND

Fluids held in containers such as tanks can experience contamination due to the presence of other types of fluids in the tank. For example, water can be present in aircraft fuel tanks due to factors such as the introduction of water-contaminated fuel into the tank, leaks in the tank, fueling during inclement weather, and caps or covers that are not properly secured after fueling. Water-contaminated fuel can result in poor in engine performance, and in extreme cases, can cause engine stoppage. Corrective action, such as draining the contaminated fuel from the tanks, is usually undertaken when the presence of water above a predetermined level is detected.

SUMMARY

Methods and systems detect the presence of a fluid, such as water, based on a reflection of optical energy from the fluid. Methods and systems also determine the concentration of a constituent element in a mixture based on a reflection of optical energy from the mixture.

Methods comprise transmitting optical energy through an optical fiber having an end face immersed in a fluid; measuring an intensity of a reflection of the optical energy from an interface of the end face and the fluid; and determining an amount of water present in the fluid based on a predetermined relationship between the intensity of the reflection and the amount of water present in the fluid.

Other methods comprise illuminating an interface of an optical fiber and a mixture of fluids with optical energy, and determining a concentration of at least one of the fluids in the mixture based on a reflection of the optical energy from the interface.

Other methods comprise directing optical energy at a fluid, and determining relative amounts of constituent elements of the fluid based on a predetermined relationship between the relative amounts of the constituent elements and an intensity of a reflection of the optical energy.

Embodiments of systems comprise a source of optical energy, a detector of optical energy, and an optical fiber in optical communication with the source of optical energy and the detector of optical energy. The optical fiber has an end face capable of being immersed in a mixture of two or more fluids. Embodiments of systems also comprise a computing device communicatively coupled to the detector of optical energy. The computing device determines a concentration of at least one of the fluids in the mixture based on a refection of the optical energy from an interface of the optical fiber and the mixture.

Other embodiments of systems comprise an optical fiber; a source of optical energy in optical communication with the optical fiber; and a detector of optical energy in optical communication with the optical fiber so that the detector of optical energy measures an intensity of a reflection of the optical energy from an interface of an end face of the optical fiber and a fluid. Embodiments also comprise a computing device communicatively coupled to the detector of optical energy. The computing device determines a concentration of water in the fluid based on a predetermined relationship between the concentration of water in the fluid and the intensity of the reflection.

Other methods comprise transmitting optical energy through an optical fiber having an end face located in a container; measuring an intensity of a reflection of the optical energy from the end face of the optical fiber; and detecting the presence of water in the container based on the intensity of the reflection.

BRIEF DESCRIPTION OF THE DRAWINGS

The foregoing summary, as well as the following detailed description of embodiments, are better understood when read in conjunction with the appended diagrammatic drawings. For the purpose of illustrating the embodiments, the drawings diagrammatically depict specific embodiments. The appended claims are not limited, however, to the specific embodiments disclosed in the drawings. In the drawings:

DETAILED DESCRIPTION OF ILLUSTRATIVE EMBODIMENTS

FIGS. 1-10 depict an embodiment of a system 10 for detecting the presence of, and determining the concentration of a fluid in a container such as a tank 12. The system 10 can be used to detect the presence of water in solution with another fluid in the tank such as Jet A aircraft fuel. The system 10 can also be used to detect the presence of water that has settled to the bottom of the tank 12 to form a separate layer of liquid water or ice below the fuel-water mixture.

Figure 1:
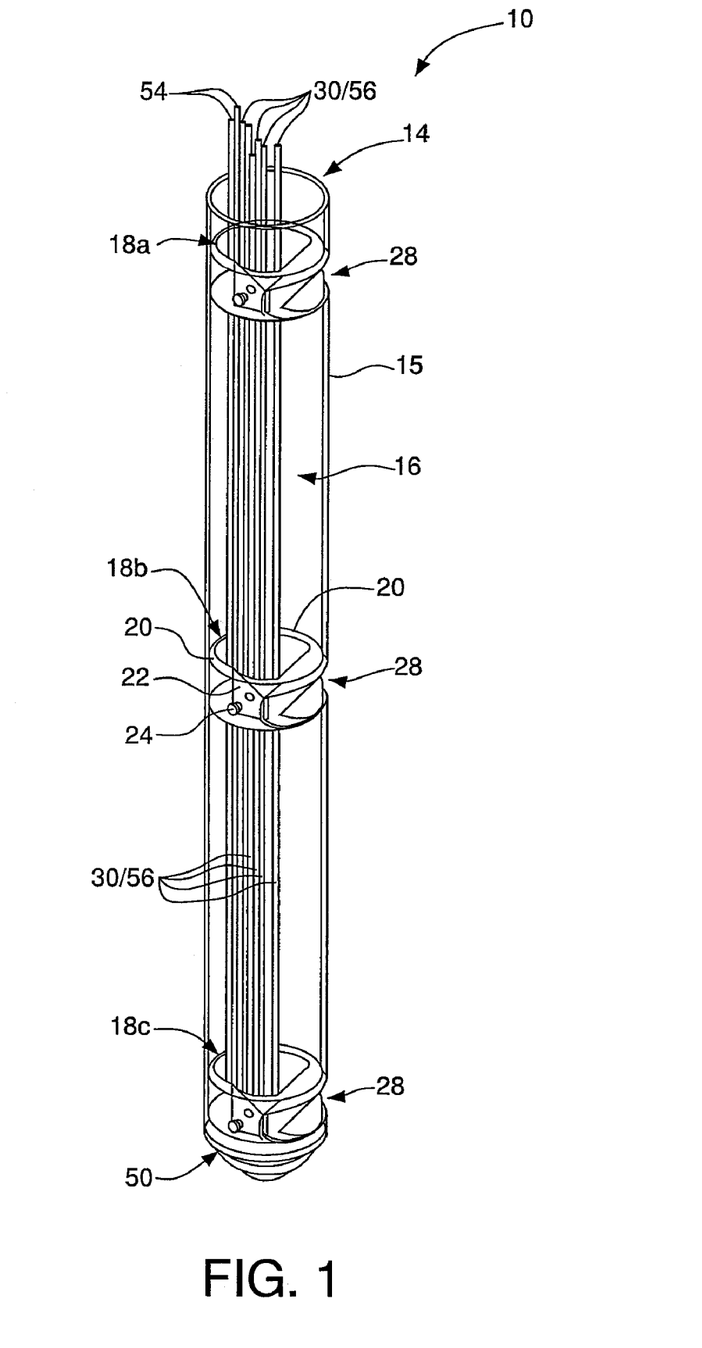
FIG. 1 is a perspective view of a housing of a system for detecting and/or determining the concentration of a fluid.
Figure 2:
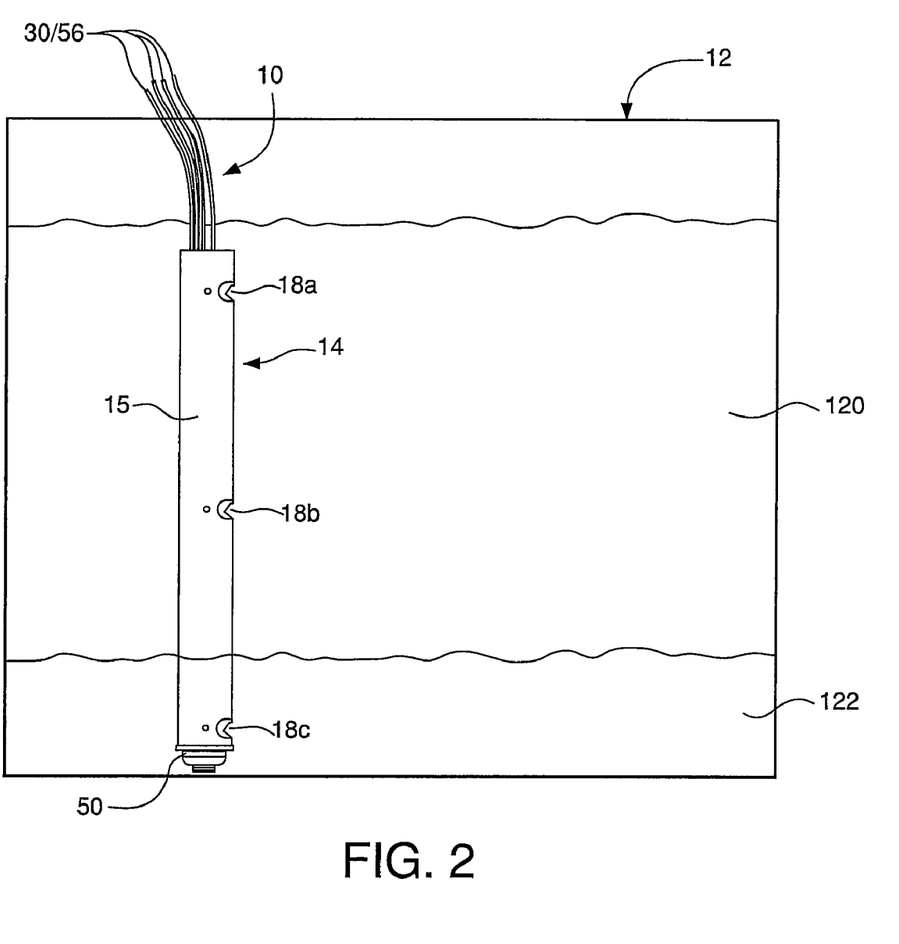
FIG. 2 is a side view of the housing shown in FIG. 1 installed in a tank.
Figures 3, 4:
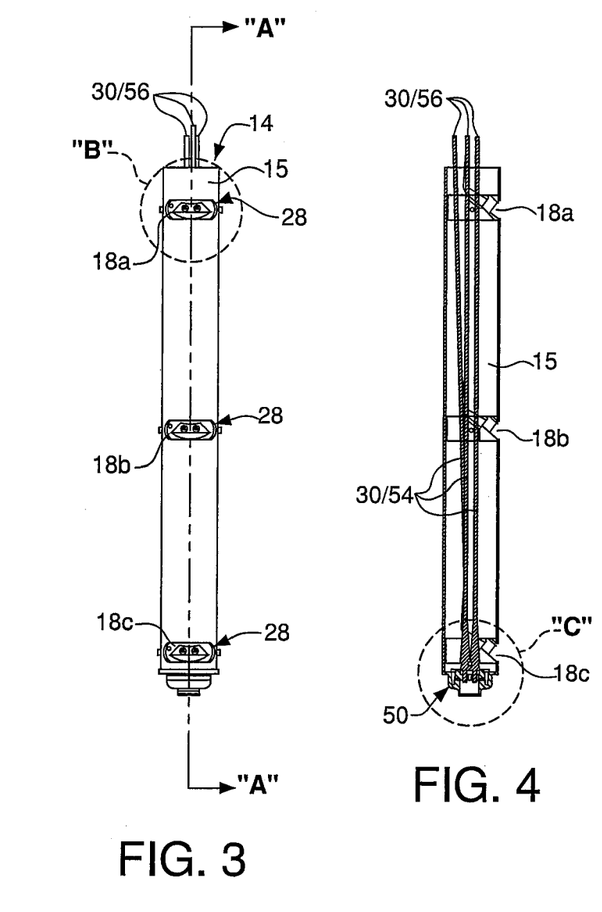
FIG. 3 is a side view of the housing shown in FIGS. 1 and 2, from a perspective rotated approximately ninety degrees from the perspective of FIG. 2.
FIG. 4 is a cross-sectional view of the housing shown in FIGS. 1-3, taken through the line "A-A" of FIG. 3.

The system 10 comprises a housing 14, as shown in FIGS. 1-3. The housing 14 includes a cylindrical body 15 having an interior volume 16. The housing 14 is positioned within the tank 12 during operation of the system 10 as shown in FIG. 2, so that the housing 14 is immersed in the fluid within the tank. The body 15 of the housing 14 is depicted as cylindrical for exemplary purposes only. The body 15 can have other shapes in alternative embodiments.

The housing 14 also includes three mounts 18a, 18b, 18c positioned within the interior volume 16 of the body 15, proximate the respective top, middle, and bottom of the body 15 as shown in FIGS. 1-4. Each of the mounts 18a, 18b, 18c includes a ring-shaped outer portion 20, and a body portion 22 that adjoins the outer portion 20.

Directional terms such as "top," "bottom," "upper," lower," 'above," below," etc. are used with reference to the component orientations depicted in FIGS. 1 and 2. These terms are used for illustrative purposes only, and are not intended to limit the scope of the appended claims.

Figure 5:
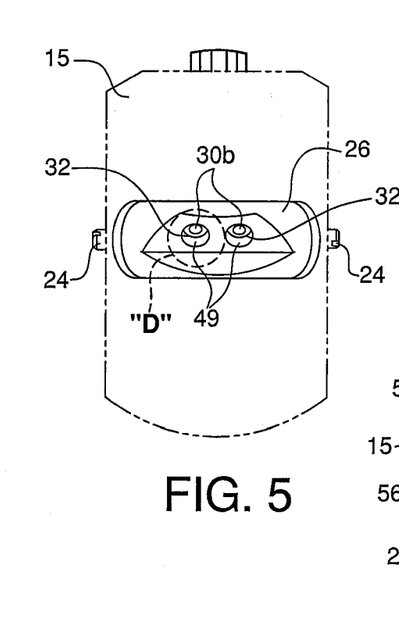
FIG. 5 is a magnified view of the area designated "B" in FIG. 3.

The mounts 18a, 18b, 18c are positioned proximate the respective top, middle, and bottom of the housing 14, as shown in FIG. 2. The outer portion 20 has a diameter slightly smaller than the inner diameter of the housing 14, so that the mounts 18a, 18b, 18c fit within the housing 14 with minimal clearance between the outer portion 20 and the inner surface of the housing 14. The mounts 18a, 18b, 18c can be secured to the housing 14 by a suitable means such as fasteners 24 that extend through the housing 14 and into the outer portion 20, as shown in FIGS. 1 and 5.

Figure 6:
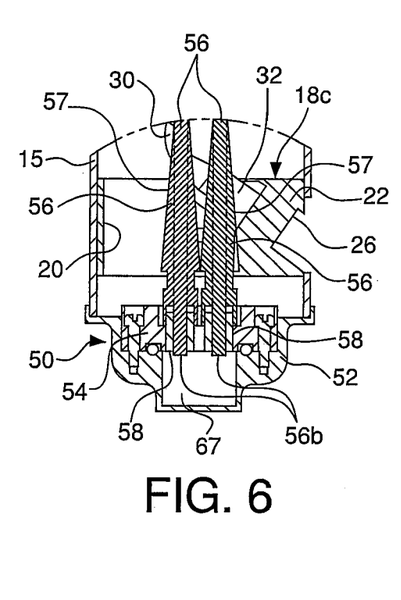
FIG. 6 is a magnified view of the area designated "C" in FIG. 4.

The body portion 22 of each mount 18a, 18b, 18c can include a substantially flat angled surface 26. The angled surface 26 is angled in relation to a longitudinal centerline of the body 15 as shown in FIG. 6, so that the angled surface 26 faces downwardly and outwardly. The housing 14 has three cutouts 28 formed therein. Each cutout 28 is positioned adjacent an associated one of the angled surfaces 26, so that the angled surfaces 26 are exposed to the environment around the housing 14 as shown in FIGS. 1-3.

The system 10 also includes a plurality of fiber optic cables 30. The system 10 also comprises a plurality of ferrules 32 depicted in FIGS. 5-7. The fiber optic cables 30 extend into the interior volume 16 as shown in FIG. 2. The ferrules 32 each receive an end 30a of an associated fiber optic cable 30. Each fiber optic cable 30 is cleaved so that an end face 30a of the fiber optic cable 30 is approximately flush with an end of the associated ferrule 32.

Figure 7:
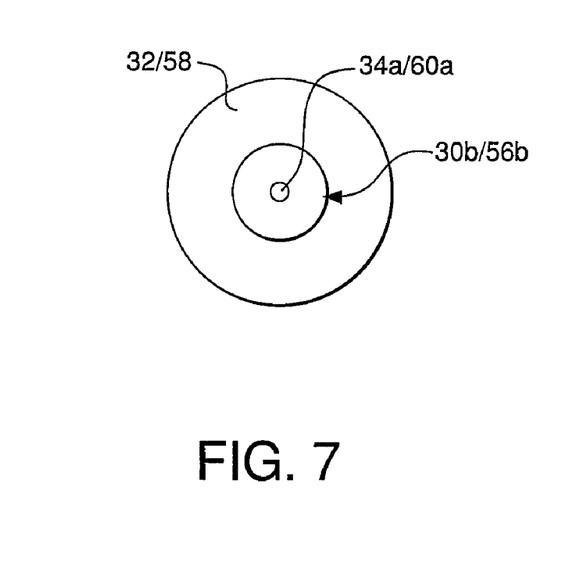
FIG. 7 is a magnified view of the area designated "D" in FIG. 5.
Figure 8:
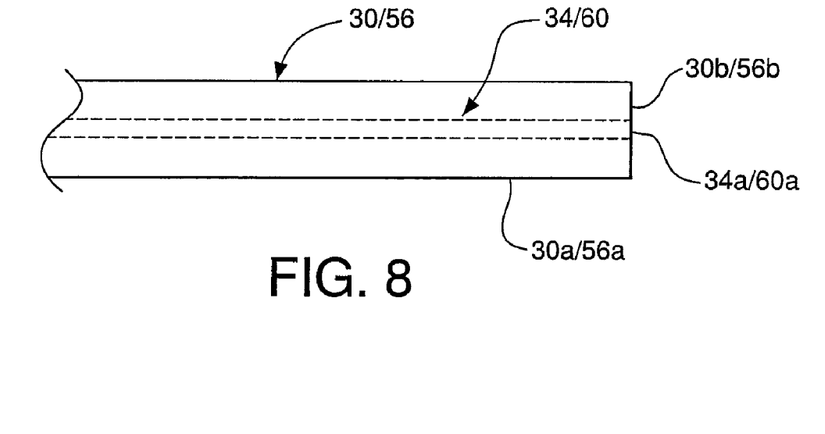
FIG. 8 is a side view of a fiber optical cable of the system shown in FIGS. 1-7.

Each fiber optic cable 30 comprises a single optical fiber 34 that functions as a waveguide. The optical fiber 34 of one of the fiber optic cables 30 is depicted in FIGS. 7 and 8. An exposed end face 34a of each optical fiber 34 is polished by a suitable technique such as lapping. The optical fibers 34 are formed from glass; optical fibers formed from materials other than glass can be used in the alternative. Alternative embodiments can include fiber optic cables having more than one optical fiber.

Two of the ferrules 32 are mounted the body portion 22 of each mount 18a, 18b, 18c. The body portion 22 of each mount 18a, 18b, 18c has two cylindrical bores 49 formed therein that receive the associated ferrules 32. The bores 49 extend inwardly form the angled surface 26, as shown in FIG. 5. The ferrules 32 can be retained in the bores 49 by a suitable means such as a press fit, an O-Ring, or an adhesive. The end faces 30b of the fiber optical cables 30 are exposed to the interior of the tank 12 when the ferrules 32 are mounted in the associated body portions 22, as shown in FIGS. 2, 5, and 6. More, or less than two ferrules 32 and two fiber optic cables 30 can be mounted on each body portion 22 in alternative embodiments.

The above-noted orientation of the angled surfaces 26 is believed to reduce the potential for debris within the tank 12 to settle on the exposed end faces 34a of the optical fibers 34. Other means for discouraging the settling of debris on the end faces 34a, such as screens that cover the end faces 34a, can also be used.

The housing 14 also includes a lower mount 50, as shown in FIGS. 1, 2, 4, and 6. The lower mount 50 comprises a cap portion 52, and a body portion 54. The cap portion 52 is mounted on the lower end of the body 15 of the housing 14 by a suitable means such as a press fit. The body portion 54 is secured to the cap portion 52 by a suitable means such as fasteners. The interface between the body portion 54 and the cap portion 52 can be sealed by a suitable means such as a gasket (not shown). The bottom of the cap portion 52 can rest on a bottom surface of the tank 12 as shown in FIG. 2.

The system 10 also comprises two fiber optic cables 56, and two ferrules 58. The ferules 58 are shown in FIGS. 6 and 7. The fiber optic cables 56 extend into the interior volume 16 as shown in FIGS. 1 and 4. The ferrules 58 each receive an end 56a of an associated fiber optic cable 56. Each fiber optic cable 56 is cleaved so that an end face 56b of the fiber optic cable 56 is approximately flush with an end of the associated ferrule 58. Each fiber optic cable 56 can be equipped with a strain-relief sleeve 57 located proximate the end 56a of the fiber optic cable 56, as shown in FIG. 6.

Each fiber optic cable 56 comprises a single optical fiber 60 that functions as a waveguide. The optical fiber 60 of one of the fiber optic cables 56 is shown in FIGS. 7 and 8. An exposed end face 60a of each optical fiber 60 is polished by a suitable technique such as lapping. The optical fibers 60 are formed from glass; optical fibers formed from materials other than glass can be used in the alternative. Alternative embodiments can include fiber optic cables having more than one optical fiber.

The ferrules 58 are mounted the body portion 54 of the lower mount 50, as shown in FIG. 6. The body portion 54 has two cylindrical bores formed therein that receive the ferrules 58. The ferrules 58 can be retained in the bores by a suitable means such as a press fit, an O-ring, or an adhesive. More, or less than two ferrules 58 and two fiber optic cables 56 can be mounted on the body portion 54 in alternative embodiments.

The cap portion 52 has a cylindrical cavity 67 defined therein, as shown in FIG. 6. The cavity 67 is located below the end faces 56b of the fiber optic cables 56 when the cap portion 52 and the body portion 54 are mated, so that the end faces 56b are exposed to the cavity 67. The cavity 67 is filled with a liquid suitable for temperature sensing. For example, the cavity 67 can be filled with optical-grade oil formulated for temperature sensing, such as MCTL oil available from Cargill Labs. This oil undergoes a relatively large change in index of refraction with changes in temperature, and therefore is particularly well suited for temperature sensing using the technique describe below. The cavity 67 is filled to its capacity with the oil, so that the oil immerses the end faces 60a of the optical fibers 60. The cavity 67 is configured so that oil can be added to the cavity 67 prior to assembly of the body portion 54 and the cap portion 52. The cavity 67 can be sealed with an O-ring (not shown) or other suitable means.

The system 10 also includes a source of optical energy. The source of optical energy can be, for example, a solid-state laser 80 depicted in FIG. 9. Other sources of optical energy, such as a light-emitting diode (LED) or an intensity-stabilized LED, can be used in the alternative.

The system 10 further includes a one-port by four-port optical splitter 82, and four three-dB optical couplers 84. Other types of optical couplers, including optical splitter/combiners, can be used in lieu of the optical couplers 84.

Figure 9:
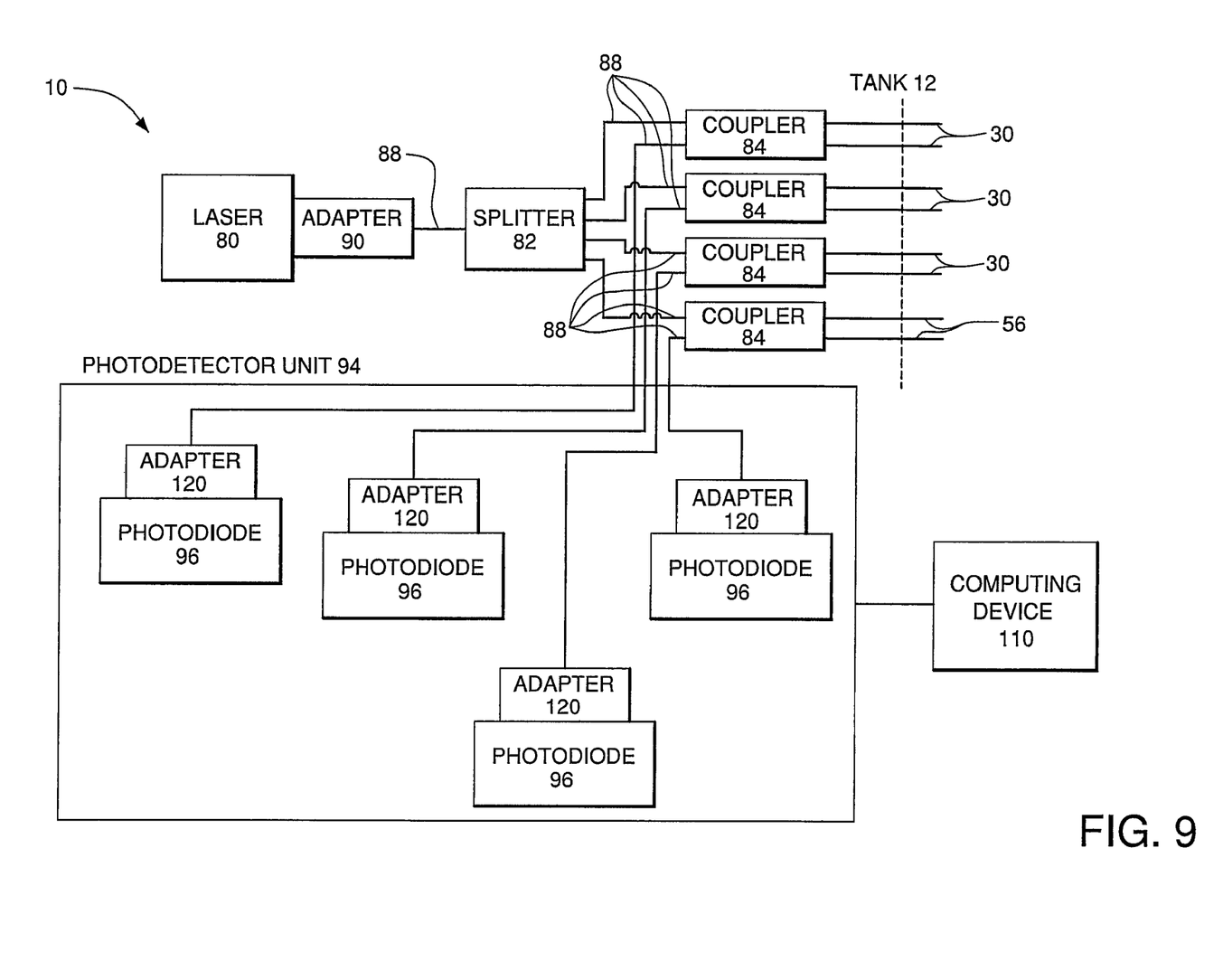
FIG. 9 is a block diagram depicting various electrical components of the system shown in FIGS. 1-8.

The optical splitter 82 is in optical communication with the laser 80 and the optical couplers 84 by way of fiber optic cables 88, as shown in FIG. 9. The laser 80 can include an adapter 90 that permits the laser 80 to be connected to an SMA connector on the fiber optic cable 88 associated with the laser 80.

The system 10 also includes a detector of optical energy such as a photodetector unit 94. The photodetector unit 94 can include four silicon photodiodes 96, as shown in FIG. 9. Other types of detectors of optical energy, such as optical power meters, avalanche photodiodes, PIN diodes, or photodiode packages with companion amplifier can be used in lieu of the photodiodes 96 in alternative embodiments.

Each of the optical couplers 84 is in optical communication with an associated one of the photodiodes 96 by way of an additional fiber optic cable 88. The photodetector unit 94 can include adapters 102 that permit each of the photodiodes 96 to be connected to an SMA connector on the associated fiber optic cable 88.

Three of the optical couplers 84 are in optical communication with an associated pair of the fiber optic cables 30, as shown in FIG. 9. The other optical coupler 84 is in optical communication with the fiber optic cables 56.

Figure 10:
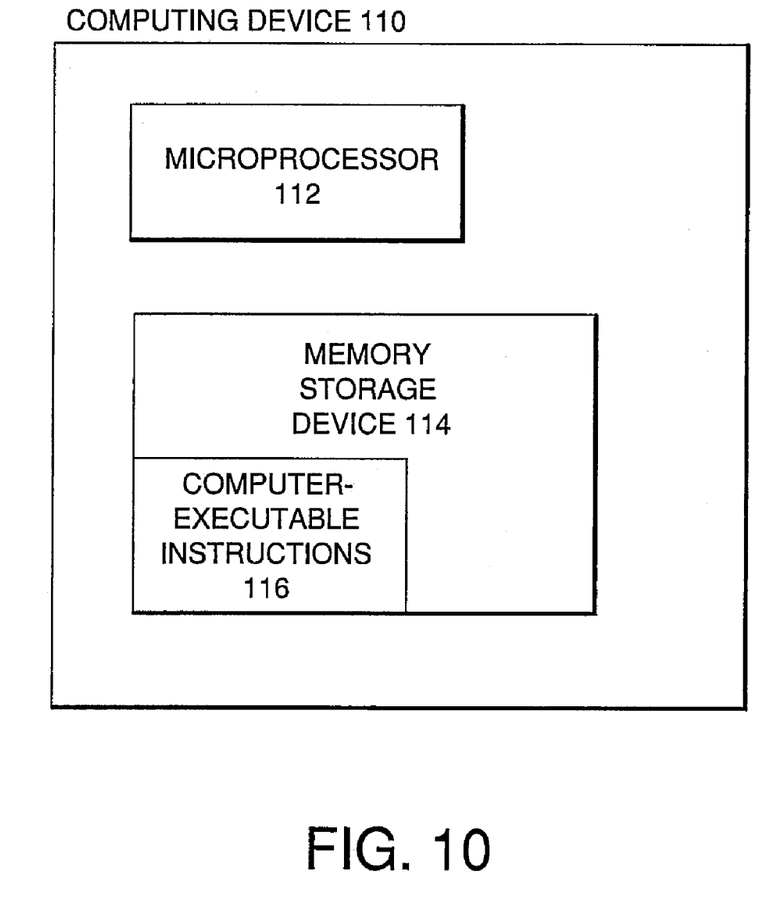
FIG. 10 is a diagrammatic illustration of the computing device shown in FIG. 9.

The system 10 further comprises a computing device 110, as shown in FIGS. 9 and 10. The computing device 110 is communicatively coupled to each of the photodiodes 96. The computing device 110 can be communicatively coupled to the laser 80, so that the computing device 110 can be used to activate and deactivate (modulate) the laser 80. The laser 80 can be activated and deactivated by other means in alternative embodiments. In embodiments in which the light source is LED based, the computing device 110 can likewise modulate the LED light source on and off. Modulation extends the life of the light source. Modulation can also be used with selective filtering in the photodetector unit 94 to facilitate filtering-out of ambient light, and pass-through of light at the frequency of the modulated light.

The computing device 110 can include a processor such as a microprocessor 112, as shown in FIG. 10. The computing device 110 can also include a memory-storage device 114 communicatively coupled to the microprocessor 112. The computing device 110 can further include a set of computer-executable instructions 116 stored on the memory-storage device 114.

The tank 12 is depicted in FIG. 2 as holding a layer of a fuel containing a certain level of water in solution therewith. This fuel-water mixture is designated with the reference character 120. The tank 12 is also depicted as holding a layer of water, designated with the reference character 122, that has settled to the bottom of the tank 12. The level of the layer of water 122 is above the mount 18c and the lower mount 50, and below the mount 18b, as shown in FIG. 2.

The end faces 34a of the optical fibers 34 of the fiber optic cables 30 are exposed to the interior volume 16 within the tank 12, as noted above. The end faces 34a of the fiber optic cables 30 associated with the mounts 18a, 18b therefore are immersed in the fuel-water mixture 120 when the fuel-water mixture 120 and the water 122 are at the levels depicted in FIG. 2. The end faces 34a of the fiber optic cables 30 associated with the mount 18c are immersed in the water 122 when the fuel-water mixture 120 and the water 122 are at the levels depicted in FIG. 2.

The computing device 110 can be programmed to generate an indication of the concentration of the water in the fuel-water mixture 120, and to detect the presence of the layer of water 122, as follows.

Optical energy in the form of light generated by the laser 80 is transmitted to the end faces 34a of the optical fibers 34 of the fiber optic cables 30 by way of the optical splitter 82, the optical couplers 84, and various ones of the fiber optic cables 86. Light generated by the laser 80 is transmitted to the end faces 60a of the optical fibers 60 of the fiber optic cables 56 by way of the optical splitter 82, the optical couplers 84, and other one of fiber optic cables 86.

The end faces 34a of the optical fibers 34 associated with the mounts 18a, 18b are exposed to the fuel-water mixture 120 by way of the associated cutouts 28 formed in the body 15 of the housing 14. The end faces 34a of the optical fibers 34 associated with the mount 18c are exposed to the water 122 by way of the associated cutout 28 formed in the body 15. The bottom mount 50 is immersed in the layer of water 122.

A Fresnel reflection is generated when optical energy such as light is incident upon the interface of two materials having different indexes of refraction. The light generated by the laser 80 thus generates Fresnel reflections when the light is incident upon the interface of the optical fibers 60 and the fuel-water mixture 120 or water 122. Fresnel reflections are likewise are generated when the light generated by the laser 80 is incident upon the oil in the cavity 67.

The reflected light is transmitted to the optical couplers 84 by the fiber optic cables 30 or the fiber optic cables 56. The reflected light within each pair of fiber optic cables 30, 50 is combined by the associated coupler 84, and transmitted to the associated photodiode 96 by the fiber optic cables 88.

Each photodiode 96 generates an electrical output proportional to the intensity of the reflected light that reaches the photodiode 96. As discussed above, detectors of optical energy other than the photodiodes 96 can be used in alternative embodiments. In applications where, for example, an optical power meter is used as the detector of optical energy, the intensity of the reflected light can be measured directly, i.e., without being converted to an electrical current as in the photodiodes 96.

The intensity of the reflected light as registered by the photodiodes 96 can be used as follows to determine the relative amounts of water and fuel in the water-fuel mixture 120, to detect the presence of the layer of water 122, and to detect the presence of ice in the tank 12.

The dielectric constant of a fluid such as Jet A fuel varies with the temperature of the fluid. An approximation of fluid index of refraction for Jet A fuel can be computed using the Maxwell's identity, as expressed in the following equation:

$$n_{(\in_r)} = \sqrt{\in_r} \qquad (1)$$

where n and $\in_r$ represent the index of refraction and the dielectric constant, respectively (see *Fundamental Insight on*

*Developing Low Dielectric Constant Polyimides*, J. O. Simpson and A. K. St. Clair NASA Langley Research Center, Hampton, Va. 23681-0001).

The Fresnel reflection coefficient represents the intensity of the optical energy reflected due to the Fresnel reflection that occurs at the interface of two materials of different indexes of refraction, per unit intensity of the optical energy incident upon the interface. When optical energy such as light is at near-normal incidence to the interface between two materials of different refractive indexes, such as a glass optical fiber and a fluid such as Jet A fuel or water, the intensity of the resulting Fresnel reflection can be calculated as follows:

$$R_s = \left(\frac{n_g - n_m}{n_g + n_m}\right)^2 \tag{2}$$

where Rs is the Fresnel reflection coefficient, $n_m$ is the index of refraction of the fluid, and $n_g$ is the index of refraction of the optical fiber.

Equation (2) can be modified as follows using the relationship between the dielectric constant and index of refraction obtained from Maxwell's identity, so that the Fresnel reflection coefficient, expressed in dB, can be calculated based on the dielectric constant of the fluid.

$$R_{s(\varepsilon_r)} = 10\log_{10}\left[\left(\frac{n_g - \sqrt{\varepsilon_r}}{n_g + \sqrt{\varepsilon_r}}\right)^2\right] \tag{3}$$

Figure 11:
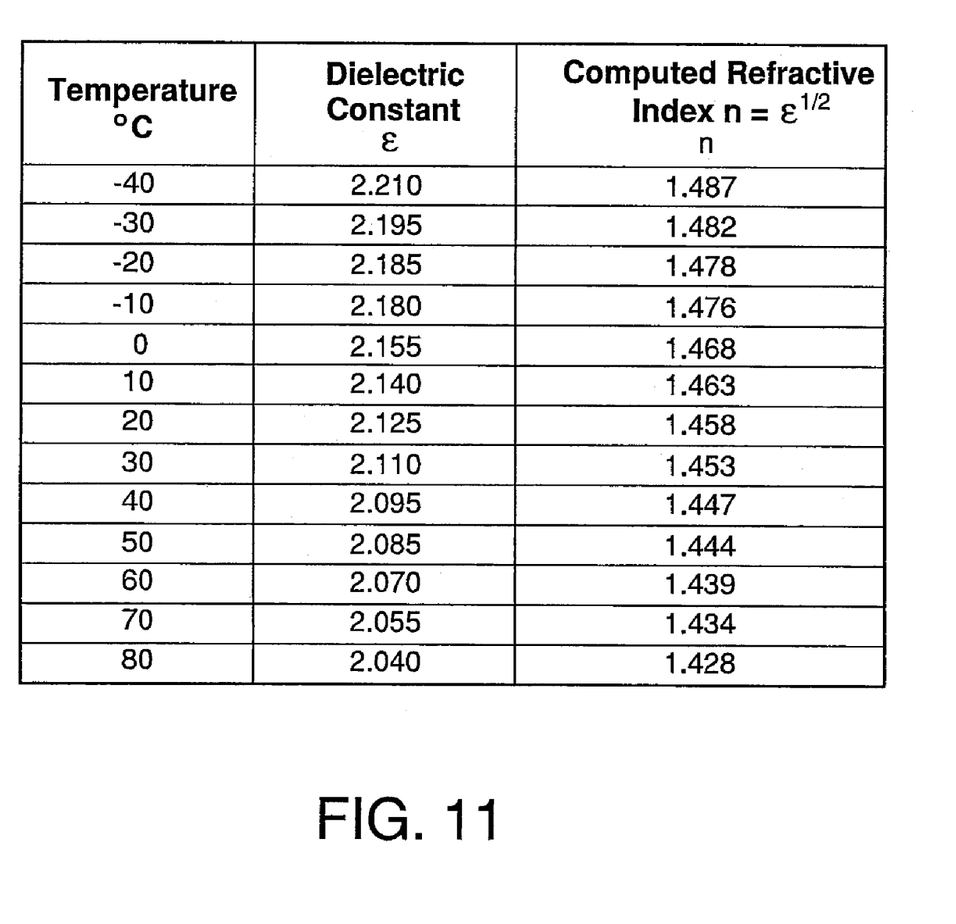
FIG. 11 is a table containing values representing the index of refraction and the dielectric constant of Jet A fuel at various temperatures between −40° C. and 80° C.

FIG. 11 is a table containing values representing the index of refraction and the dielectric constant of Jet A fuel at various temperatures between −40° C. and 80° C. The values in the table were generated using published values for the dielectric constant of Jet A fuel obtained from the Handbook of Aviation Fuel Properties, CRC, Inc., Third Printing, May 1988, and the relationship between the index of refraction and dielectric constant provided by Maxwell's identity, i.e., equation (1) above.

The index of refraction for water varies between about 1.334 at a temperature of 14° C., and about 1.325 at a temperature of about 70° C. The index of refraction of ice is about 1.331. Because the index of refraction of water is lower that that of Jet A fuel at the same temperature, a mixture of Jet a fuel and water will have a lower index of refraction that pure Jet A fuel at the same temperature.

Equation (3) above indicates that a decrease in the index of refraction of one of the materials at the reflective interface will result in an increase in the Fresnel reflection coefficient. Thus, the Fresnel reflection coefficient associated with a homogeneous mixture of water and Jet A fuel will be higher that that associated with pure Jet A fuel under comparable conditions. Equation (3) also indicates that the Fresnel reflection coefficient will increase as the percentage of water in the fuel-water mixture 120 increases. The intensity of the light reflected at the interfaces of the optical fibers 34 and the water-fuel mixture 120 or water 122 and measured by the photodiodes 96 is therefore dependent upon, and can be used to determine the relative amounts of the fuel and water present at each interface.

Figure 12:
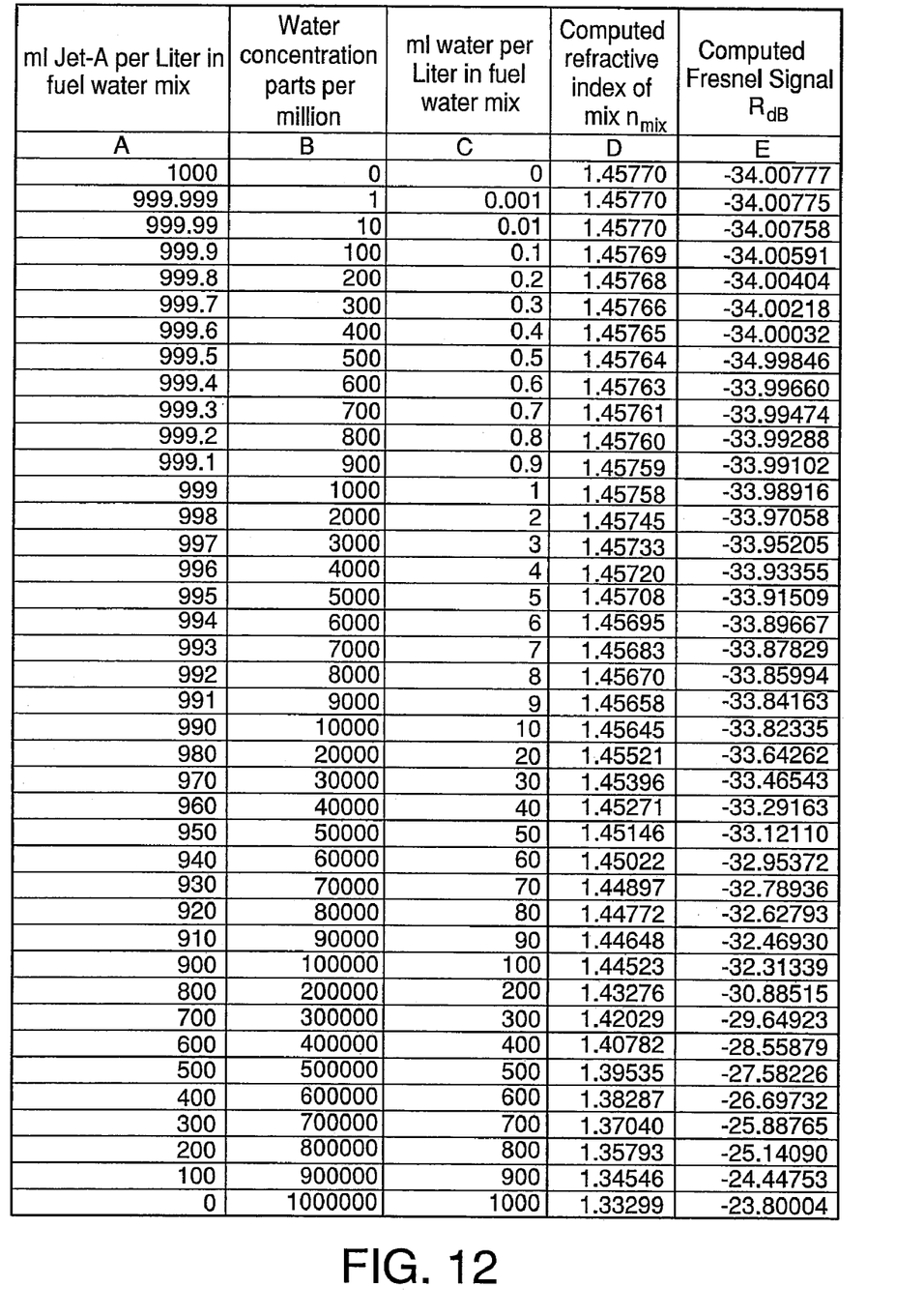
FIG. 12 is a table containing calculated values of a Fresnel reflection coefficient, expressed in dB, at the interface of a glass optical fiber and (i) substantially pure Jet A fuel; (ii) substantially pure water; and (iii) various mixtures of Jet A fuel and water, at a temperature of 20° C.

Column E of the table presented in FIG. 12 lists calculated values of the Fresnel reflection coefficient, expressed in dB, at the interface of a glass optical fiber and (i) substantially pure Jet A fuel; (ii) substantially pure water; and (iii) various mixtures of Jet A fuel and water, at a temperature of 20° C. The values of the Fresnel reflection coefficients were calculated based on equation (3) above, using the following respective values for the indexes of refraction of Jet A fuel, water, and a glass optical fiber: 1.4577; 1.3330; and 1.517.

The indexes of refraction of the various mixtures of Jet A fuel and water used in the calculation of the Fresnel reflection coefficients, listed in column D of the table, were calculated using the following equation:

$$D = \left(\frac{A(n_f) + C(n_w)}{A + C}\right) \tag{4}$$

where D is the index of refraction of the mixture; A is the amount of Jet A fuel, in milliliters, in a 1,000-ml mixture of Jet-A fuel and water, as listed in column A of the table; C is the amount of water, in milliliters, in the 1,000-ml mixture, as listed in column C; $n_f$ is the refractive index of Jet A fuel at 20° C.; and $n_w$, is the refractive index of water at 20° C.

The Fresnel reflection coefficients listed in column E of the table of FIG. 12 were calculated using the following equation:

$$E = 10\log\left(\frac{n_g - D}{n_g + D}\right)^2 \tag{5}$$

where D is the index of refraction of the mixture, as calculated using equation (4); and $n_g$ is the refractive index of a glass optical fiber.

Figure 13:
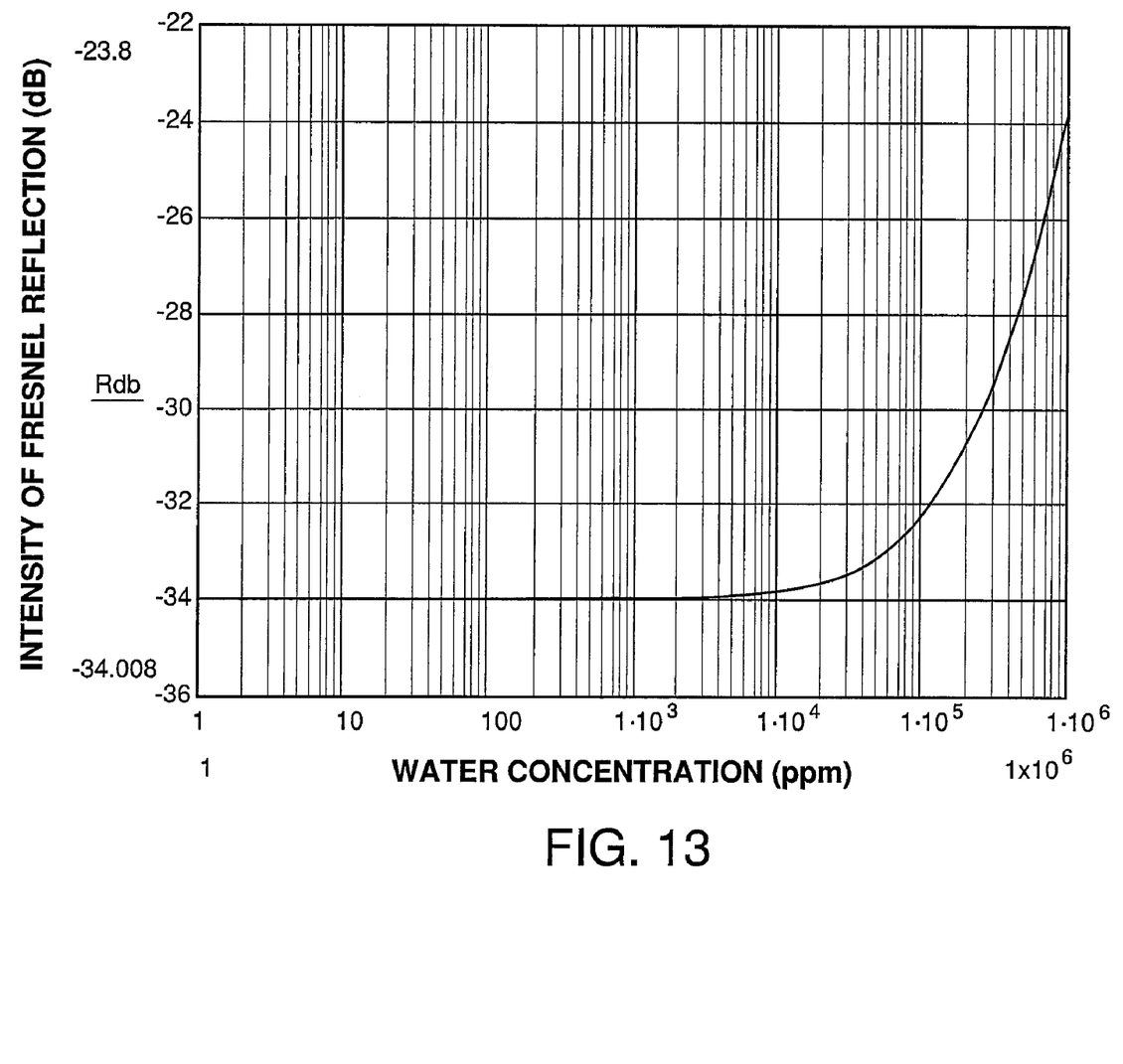
FIG. 13 is a graphical depiction of the relationship between water concentration and Fresnel reflection coefficient, generated using values from FIG. 12.

FIG. 13 is a graphical depiction of the relationship between water concentration and Fresnel reflection coefficient, generated using the values in columns "B" and "E" of FIG. 12. FIG. 13 indicates that the changes in the Fresnel reflection coefficient caused by changes in the water concentration level are sufficient to permit the Fresnel reflections associated with different water-concentration levels to be differentiated using commercially-available equipment, once the water-concentration level reaches approximately 10,000 ppm.

The computing device 110 can be configured to provide an estimate of the amount of water present in the fluid within the tank 12 based on the outputs of the photodiodes 96, and predetermined information such as that presented in FIG. 11.

The Fresnel reflection coefficient, as discussed above, represents the intensity of the light reflected due to the Fresnel reflection that occurs at the interface of two materials of different indexes of refraction, per unit intensity of the optical energy incident upon the interface.

The intensity of the light associated with the Fresnel reflections generated at the end faces 34a of the optical fibers 34 of each pair of fiber optic cables 30 is measured by the associated photodiodes 96, and is communicated to the computing device 110 as an electrical input from each photodiode 96.

Using the splitter/combiner configuration shown in FIG. 9, the combined intensity of the light reaching the end faces 34a of the optical fibers 34 of each pair of fiber optic cables 30 is approximately equal to one-fourth of the intensity of the light generated by the laser 80, due to the effect of the four-way optical splitter 82. The splitter/combiner configuration of FIG. 9 is disclosed for exemplary purposes only; other splitter combiner combinations can be used in the alternative.

Equation 2 describes the fraction of incident light reflected at the end faces 34a of the optical fibers 34. The intensity of the light reaching each of the end faces 34a is not critical as long as the intensity of the light source is stable, since the operation of the system 10 is based on the measured intensity of the reflected light. With a stable light source, the detected signal depends primarily on changes in the reflected signal due to changes in index of refraction of the fluid in which the end faces 34a are exposed. In a practical implementation, a slight variation of incident light at each pair of end faces 34a due to performance variations of an individual splitter 82 and coupler 84 would be automatically accounted for during calibration of the system 10. A measure of the reflected signal for a given fluid at a given temperature for each pair of end faces 34a would be recorded during the calibration. The calibration would remain constant as long as the light source is stable.

Tables such as the table depicted in FIG. 12 can be generated for various temperatures within the range of operating temperatures of the system 10. The tables can be stored in the memory-storage device 114 of the computing device 110. For example, tables can be generated for temperatures ranging from −40° C. to 80° C., in increments of 1° C. These tables would represent the results of the calibration of the system 10 as discussed above.

The computing device 110 can be programmed to estimate the concentration of water in the fluid within the tank 12 by looking up the water concentration value corresponding to the Fresnel reflection coefficient calculated as discussed above, using the table corresponding to the temperature of the mixture. The temperature of the mixture can be determined in the manner discussed below.

The system 10 can further include a display (not shown) communicatively coupled to the computing device 110. The water-concentration and temperature estimates generated by the computing device 110 can be transmitted to the display. The water-concentration and temperature estimates information can be transmitted to other devices, such as a remote computer, for further processing, display, or storage.

Figure 14:
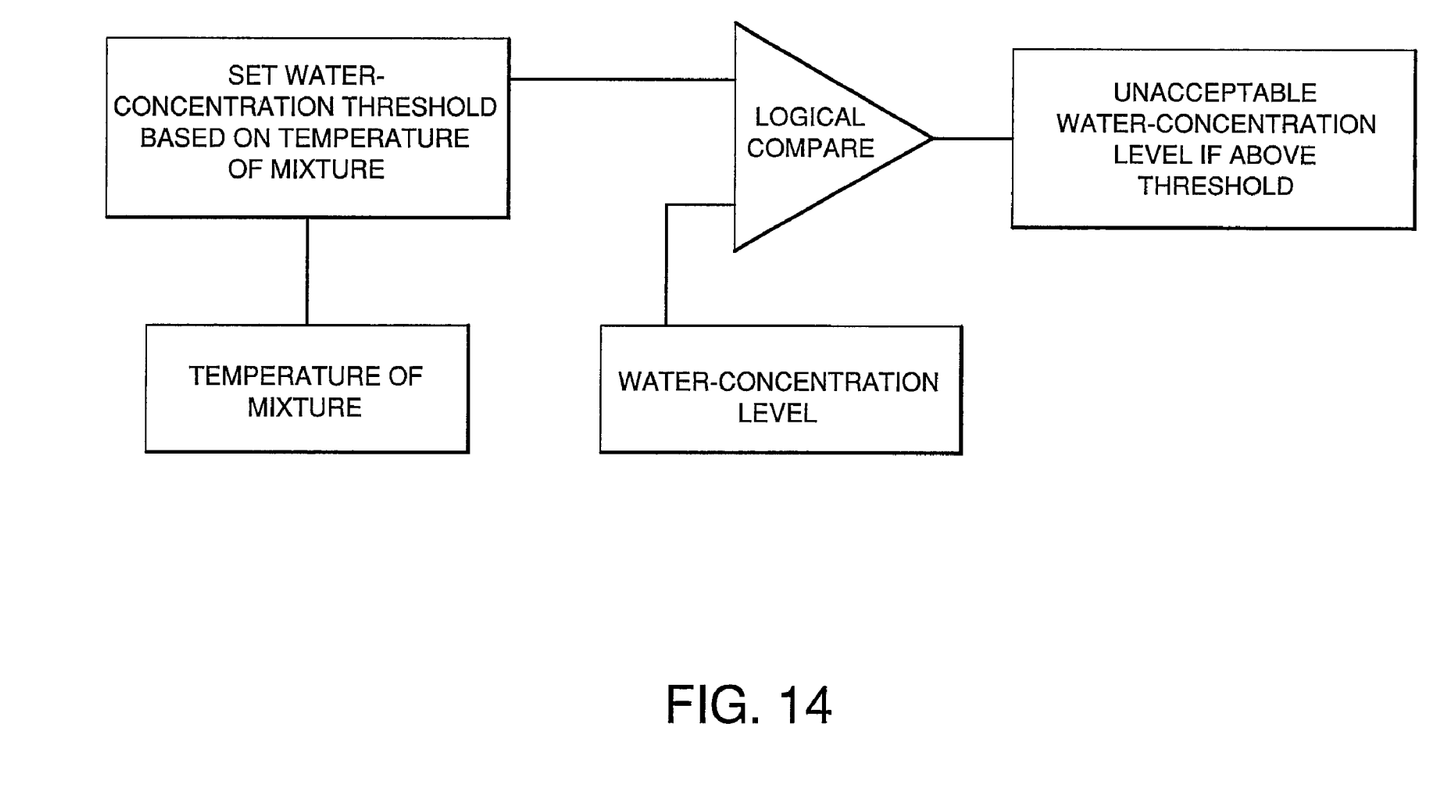
FIG. 14 is a logic diagram depicting logic that can be input to a computing device of the system shown in FIGS. 1-10.
Figure 15A:
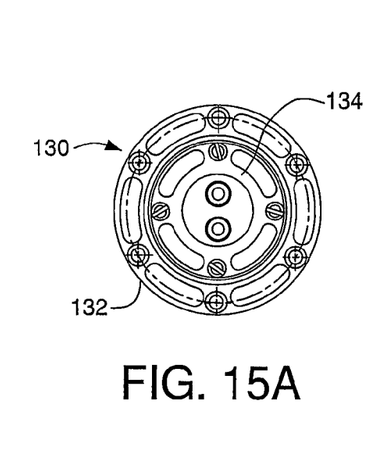
FIG. 15A is a top view of a variant of a lower mount of the system shown in FIGS. 1-10.
Figure 15B:
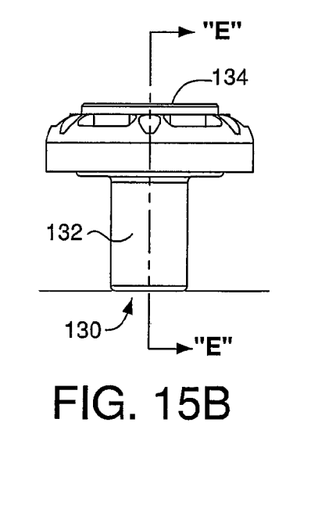
FIG. 15B is a side view of the lower mount shown in FIG. 15A.
Figure 15C:
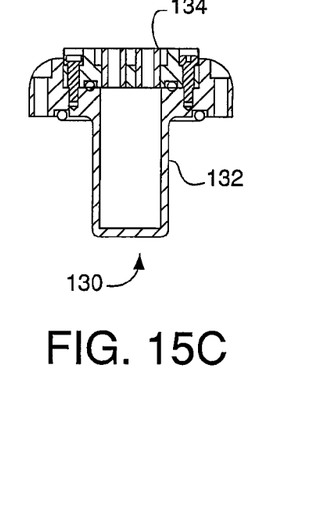
FIG. 15C is a cross-sectional view of the lower mount shown in FIGS. 15A and 15B, taken through the line "E-E" of FIG. 15B.
Figure 15D:
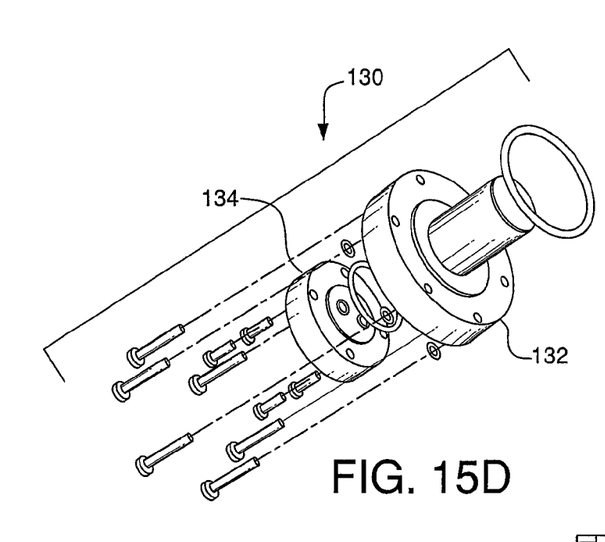
FIG. 15D is an exploded view of the lower mount shown in FIGS. 15A-15C.

The computing device 110 or the remote computer can be programmed to activate an alarm, caution light, or other warning means when the water concentration is above a predetermined value. For example, in a situation where the lowermost pair of end faces 34a, i.e., the end faces associated with the mount 18c, are immersed in a fluid at a temperature of about 20° C., and the signal detected at the photodiode 96 associated with those end faces 34a increases by about 1.8 dB from a reference level indicative of the presence of pure fuel, an alarm can be activated by the computing device 110 indicating a water-concentration level approaching or exceeding 10,000 parts per million (based on the data presented in FIG. 12). Logic for this alarm methodology is depicted in FIG. 14.

The computing device 110 or remote computer can also be programmed to recognize the presence of a layer of substantially pure water, such as the layer of water 122, in combination with a temperature reading at or below the freezing point of water, as an indication that ice is likely present in the tank 12. The computing device 110 or remote computer can be programmed to generate a warning or other indication signaling the possibility of ice in the tank 12 under such circumstances.

It is expected that the above-noted ice detection, under most circumstances, would be performed based on Fresnel reflections from the lowermost end faces 34a, i.e., the end faces 3a associated with the mount 18c, while the uppermost and middle end faces 34a would be used to provide an indication of the concentration of water in a fuel-water mixture 120.

The fiber optic cables 56 are used to measure the temperature of the fluid or fluids within the tank 12. The end faces 60a of the optical fibers 60 of the fiber optic cables 56 are immersed in the oil within the cavity 67, as discussed above. The oil will remain at approximately the same temperature as the fuel-water mixture 120 and the layer of water 122 once the temperatures of the fuel-water mixture 120, the water layer 122, and the oil have stabilized.

Fresnel reflections are generated at the interface of each optical fiber 60 and the oil in the cavity 67 when the light generated by the laser 80 is incident upon the interface. The reflected light is transmitted to the photodiode 96 associated with the fiber optic cables 56 by way of the associated optical coupler 84 and fiber optic cable 88.

The intensity of each Fresnel reflection generated at the end faces 68a of the optical fibers 60 is related to the temperature of the oil in the cavity 67. The response of the system 10 to variations in the temperature of the oil can be calibrated prior to operation of the system 10. The results of the calibration can be programmed into the computing device 110, so that the computing device 110 can interpret a particular input from the photodiode 96 associated with the fiber optic cables 56 as an indication that the oil 68 is at a particular temperature.

If the fluid or fluids in the tank 12 experience a detectable change in refractive index with changes in temperature, it is possible to expose the end faces 56b of the fiber optic cables 56 directly to the fluids within the tank 12; such alternative embodiments can be constructed without the cavity 67.

Further details concerning the above-described temperature-measurement technique can be found in U.S. application titled "Methods and Systems for Determining the Density and/or Temperature of Fluids," filed on Jan. 3, 2007 with Ser. No. 11/649,109, the contents of which is incorporated by reference herein in its entirety.

The use of the above-noted technique for determining the temperature of the fluid or fluids within the tank 12 is described for exemplary purposes only. Other temperature-measurement techniques can be used in the alternative.

The system 10 does not introduce electrical current into the fluids or the tank 12. The system 10 therefore does not introduce the potential for an explosion caused by the presence of a spark in or near the fluids. The system 10 can thus be used to determine the level and/or types of volatile, flammable fluids within a tank or other type of container, without introducing the potential to ignite flammable vapors of the fluid that may be present within the enclosed volume.

The foregoing description is provided for the purpose of explanation and is not to be construed as limiting. While the embodiments have been described with reference to specific embodiments or methods, it is understood that the words which have been used herein are words of description and illustration, rather than words of limitation. Furthermore, although particular embodiments and methods have been described herein, the appended claims are not intended to be limited to the particulars disclosed herein. Those skilled in the relevant art, having the benefit of the teachings of this specification, may effect numerous modifications to the embodiments and methods as described herein, and changes may be made without departing from the scope of the appended claims.

For example, specific details of the housing 16 have been presented for exemplary purposes only. The end portions 30a of the fiber optic cables 30 can be mounted in housings substantially different than the housing 16. More, or less than three of the mounts 18a, 18b, 18c and six of the fiber optic cables 30 can be used in alternative embodiments. Other alternative embodiments can be constructed without a housing. In particular, the ferrules 32 that house the end portions 30a of the fiber optic cables 30 can be mounted directly on the tank 12, or on a probe or mounting designed for portability or ease in being moved between multiple tanks 12.

Variations in the configurations of the light source and light detectors are possible in alternative embodiments. For example, alternative embodiments can include multiple light sources. Each light source can be in optical communication with an associated one of the optical couplers 98. Other alternative embodiments can include a single light detector. The single light detector can be placed in optical communication with the optical couplers 98 on a sequential basis, using an optical switch. Other variations in the configurations of the light source and light detectors are also possible.

The operation of the system 10 has been described in connection with the fuel-water mixture 120 and the layer of water 122 for exemplary purposes. The system 10 can be configured to detect the presence of water, or other types of fluids, in fluids other than Jet A fuel.

FIGS. 15A-15D depict an alternative embodiment of the lower mount 50 in the form of a lower mount 130 comprising a cap portion 132 and a body portion 134. The cap portion 132 defines a cavity 136 for holding the temperature-sensing oil. The lower mount 130 is substantially similar to the lower mount 50, with the exception that the cavity 136 is elongated in comparison to the cavity 67 of the lower mount 50.

Figure 16A:
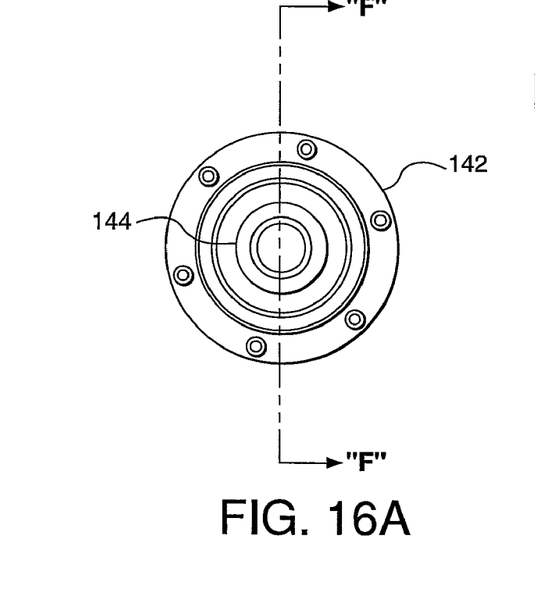
FIG. 16A is a top view of another variant of a lower mount of the system shown in FIGS. 1-10.
Figure 16B:
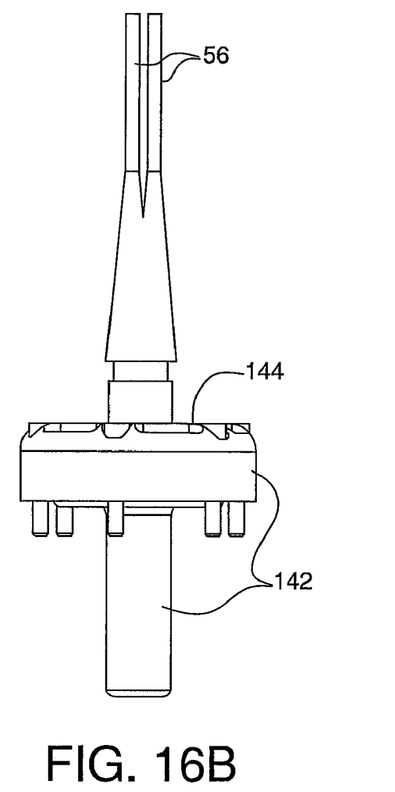
FIG. 16B is a side view of the lower mount shown in FIG. 16A.
Figure 16C:
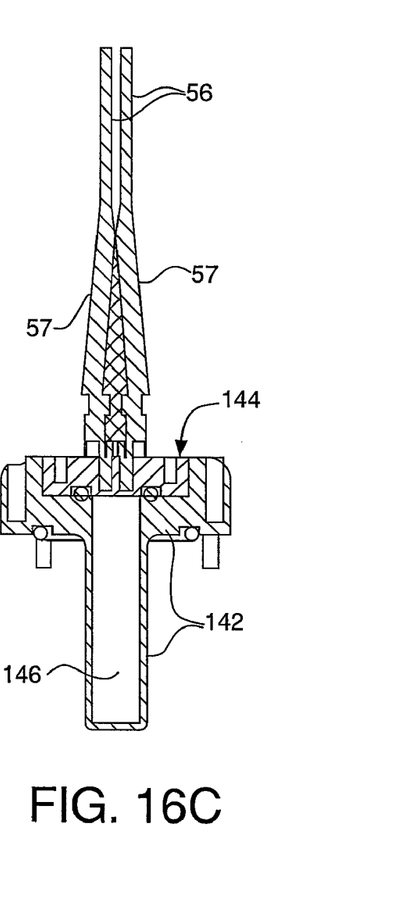
FIG. 16C is a cross-sectional view of the lower mount shown in FIGS. 16A and 16B, taken through the line "F-F" of FIG. 16B.

FIGS. 16A-16C depict another alternative embodiment of the lower mount 50 in the form of a lower mount 140 comprising a cap portion 142 and a body portion 144. The cap portion 142 defines a cavity 146 for holding the temperature-sensing oil. The lower mount 140 is substantially similar to the lower mount 50, with the exception that the cavity 146 is elongated in comparison to the cavity 67 of the lower mount 50.

It is believed to be possible to detect the presence or the concentration of a third fluid in a mixture, provided the presence of a third fluid produces a monotonic response at the photodiode 96 associated with the pair of end faces 34a immersed in the fluid. For example, if the presence of a third fluid in a mixture of a first, a second, and the third fluid drives the output of the associated photodiode 96 above or below the expected response for a mixture containing only the first and second fluids, then the response would be monotonic and a calibration curve could be developed. In this case the presence of the third fluid could be detected by the system 10.

What is claimed is:

1. A method, comprising:
   transmitting optical energy through an optical fiber having an end face immersed in a fluid;
   measuring an intensity of a reflection of the optical energy from an interface of the end face and the fluid; and
   determining an amount of water present in the fluid based on a predetermined relationship between the intensity of the reflection and the amount of water present in the fluid;
   determining a temperature of the fluid, and
   wherein determining a temperature of the fluid comprises determining the temperature of the fluid based on an intensity of a reflection of optical energy from an interface of another optical fiber and another fluid having a temperature approximately equal to the temperature of fluid.

2. The method of claim 1, wherein determining an amount of water present in the fluid based on a predetermined relationship between the intensity of the reflection and the amount of water present in the fluid comprises determining the amount of water present in the fluid based on a predetermined relationship between the intensity of the reflection, the amount of water present in the fluid, and the temperature of the fluid.

3. The method of claim 1, wherein transmitting optical energy through an optical fiber having an end face immersed in a fluid comprises transmitting the optical energy from a laser.

4. The method of claim 1, wherein measuring an intensity of a reflection of the optical energy from an interface of the end face and the fluid comprises measuring the intensity of the reflection using a photodiode.

5. The method of claim 1, wherein determining an amount of water present in the fluid based on a predetermined relationship between the intensity of the reflection and the amount of water present in the fluid comprises determining the amount of water present in the fluid based on information relating the intensity of the reflection per unit intensity of the optical energy incident upon the interface of the end face and the amount of water present in the fluid.

6. The method of claim 1, wherein transmitting optical energy through an optical fiber having an end face immersed in a fluid comprises transmitting the optical energy through an optical fiber having an end face immersed in a mixture of fuel and water.

7. The method of claim 1, further comprising determining whether ice is present based on the amount of water present in the fluid and the temperatures of the fluid.

8. A method, comprising:
   illuminating an interface of an optical fiber and a mixture of fluids with optical energy; and
   determining a concentration of at least one of the fluids in the mixture based on a reflection of the optical energy from the interface,
   wherein determining a concentration of at least one of the fluids in the mixture based on a reflection of the optical energy from the interface comprises determining the concentration based on a predetermined relationship between an intensity of the reflection of the optical energy from the interface and the concentration,
   determining a temperature of the mixture, and
   wherein determining a temperature of the mixture comprises directing optical energy at an end face of another optical fiber having an end face immersed in another fluid having a temperature approximately equal to the temperature of the mixture.

9. The method of claim 8, further comprising measuring the intensity of the reflection.

10. The method of claim 9, wherein measuring the intensity of the reflection comprises measuring the intensity of the reflection using a photodiode.

11. The method of claim 8, wherein determining a concentration of at least one of the fluids in the mixture based on a reflection of the optical energy from the interface comprises determining the concentration based on a predetermined relationship between the intensity of the reflection of the optical energy from the interface, the concentration, and the temperature of the mixture.

12. The method of claim 8, wherein illuminating an interface of an optical fiber and a mixture of fluids with optical energy comprises transmitting the optical energy to the interface from a light source.

13. The method of claim 8, wherein illuminating an interface of an optical fiber and a mixture of fluids with optical energy comprises illuminating an interface of the optical fiber and a mixture of fuel and water.

14. The method of claim 8, further comprising determining a temperature of the mixture, and determining whether ice is present in the mixture based on the temperature of the mixture and the concentration of the water.

15. A method, comprising:

illuminating with optical energy an interface between an optical fiber and a fluid mixture including fuel and water in a fuel tank;

monitoring a concentration level of the water in the fluid mixture based on a reflection of the optical energy from the interface, determining a temperature of a fluid in the fluid mixture, and generating a warning or other indication as to the possibility of ice in the fuel tank based on a recognition of a presence of substantially pure water during the monitoring of the concentration level of the water in combination with a determined temperature representing a temperature at or below the freezing temperature of the substantially pure water for the conditions presented in the fuel tank.

16. The method of claim 15 wherein there is illuminated with optical energy a plurality of interfaces between respective optical fibers and the fluid mixture, and wherein the interfaces are spaced apart in height within the fuel tank in a manner in which a lower positioned interface is used in the detection of a layer of the determined substantially pure water formed in the fuel tank while an above positioned interface is used in the detection of a concentration of a fluid in a fuel-water mixture positioned above the layer of substantially pure water.

17. The method of claim 16 further comprising generating a water concentration warning when the concentration of water relative to pure fuel is deemed to meet or exceed a predetermined level.

18. The method of claim 17 wherein the predetermined level is 10,000 parts per million or above.

19. The method of claim 15 wherein the generating of a warning or other indication includes generating a signal based on a determination of a computing device which is used to recognize a situation wherein there is both a sufficiently pure water concentration and sufficiently low enough temperature as to indicate the possibility of ice in the fuel tank.

20. The method of claim 15 further comprising generating a water concentration warning when the concentration of water relative to pure fuel is deemed to meet or exceed a predetermined level.

21. The method of claim 15 wherein there is illuminated with optical energy a plurality of interfaces between respective optical fibers and the fluid mixture, and wherein the interfaces include a lower, an intermediate and an upper interface that are spaced apart in height within the fuel tank in a manner in which a lower positioned interface is used in the detection of a layer of the determined substantially pure water formed in the fuel tank, while the intermediate and upper interfaces are used in the detection of a concentration of water in a fuel-water mixture positioned above the layer of substantially pure water.

22. The method of claim 15 wherein there are a plurality of interfaces comprised of fiber optic end faces that are arranged as vertically spaced apart sets of two adjacent fiber optic end faces in contact with the fluid mixture.

* * * * *